(12) United States Patent
Toyama et al.

(10) Patent No.: US 10,392,547 B2
(45) Date of Patent: Aug. 27, 2019

(54) SUPER-COOLING RELEASE MATERIAL AND METHOD FOR PRODUCING SAME

(71) Applicant: DENSO CORPORATION, Kariya, Aichi-pref. (JP)

(72) Inventors: Yasuhiro Toyama, Kariya (JP); Mika Kawakita, Kariya (JP); Katsunori Iwase, Kariya (JP); Hajime Shingai, Kariya (JP); Hiroyuki Kumano, Yokohama (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 132 days.

(21) Appl. No.: 15/520,172

(22) PCT Filed: Nov. 12, 2015

(86) PCT No.: PCT/JP2015/005644
§ 371 (c)(1),
(2) Date: Apr. 19, 2017

(87) PCT Pub. No.: WO2016/075941
PCT Pub. Date: May 19, 2016

(65) Prior Publication Data
US 2017/0342305 A1 Nov. 30, 2017

(30) Foreign Application Priority Data

Nov. 14, 2014 (JP) .................................. 2014-231287
May 25, 2015 (JP) .................................. 2015-105672
Oct. 23, 2015 (JP) .................................. 2015-209259

(51) Int. Cl.
C09K 5/06 (2006.01)
C07C 211/63 (2006.01)
C08K 3/08 (2006.01)

(52) U.S. Cl.
CPC ............ C09K 5/063 (2013.01); C07C 211/63 (2013.01); C08K 3/08 (2013.01); Y02E 60/147 (2013.01)

(58) Field of Classification Search
CPC .. C09K 5/063; C09K 5/06; C08K 3/08; C07C 211/63; Y02E 60/147
USPC ............................................. 252/67, 68, 69
See application file for complete search history.

(56) References Cited

U.S. PATENT DOCUMENTS

| | | | | |
|---|---|---|---|---|
| 4,332,690 | A * | 6/1982 | Kimura | C09K 5/063 165/10 |
| 2002/0189277 | A1* | 12/2002 | Takao | C09K 5/00 62/430 |
| 2010/0133464 | A1* | 6/2010 | Tomura | C09K 5/063 252/70 |
| 2016/0370084 | A1* | 12/2016 | Bessho | C09K 5/063 |
| 2017/0226394 | A1* | 8/2017 | Ide | C09K 5/063 |

FOREIGN PATENT DOCUMENTS

| | | | | |
|---|---|---|---|---|
| JP | 2007161893 A | | 6/2007 | |
| WO | WO-2015076095 A1 | * | 5/2015 | ............ C09K 5/063 |
| WO | WO-2018198848 A1 | * | 11/2018 | |

OTHER PUBLICATIONS

X.J.Shi et al., "A comparative study of different methods for the generation of tetra-n-butyl ammonium bromide clathrate hydrate slurry in a cold storage air-conditioning system", Applied Energy, 112 (2013), 1393-1402. (Year: 2013).*
Kumano, Hiroyuki et al., "Experimental study on effect of electric field on hydrate nucleation in supercooled tetra-n-butyl ammonium bromide aqueous solution", International Journal of Refrigeration 35 (2012) p. 1266.
Asplund, Milja et al., "Crystal Structures of Tetrabutylammonium Dichlorocuprate(I) and Tetrabutylammonium Dibromocuprate(I), $[N(C_4H_9)4][CuCl_2]$ and $[N(C_4H_9)_4][CuB_r2]$", Acta Chemica Scandinavica A 37 (1983), p. 57-62.
Nilsson, Martin, "Tetrabutylammonium Inorganocuprates(I)*— $Bu_4N^+CuCl_2^-CuBr_2^-$, $CuI_2^-$ and $Cu(CN)_2^-$", Acta Chemica Scandinavica B 36 (1982), p. 125-126.
Rodionova, Tatyana V. et al., "Calorimetric and Structural Studies of Tetrabutylammonium Bromide Ionic Clathrate Hydrates", The Journal of Physical Chemistry B 2013, 117, p. 10677-10685.

* cited by examiner

*Primary Examiner* — Douglas J McGinty
(74) *Attorney, Agent, or Firm* — Harness, Dickey & Pierce, P.L.C.

(57) ABSTRACT

A supercooling release material, which releases a supercooled state of a cold storage material including one or more types of alkylammonium halide aqueous solutions that generate a hydrate by being cooled to a hydrate generation temperature or lower, includes: an alkylammonium ion included in the cold storage material; and a metal halide ion which has, as a constituent element, a halogen element included in the cold storage material. The supercooled state of the cold storage material can be reliably released by using the supercooling release material having such a configuration.

10 Claims, 9 Drawing Sheets

FIG. 6

| ELECTRODE MATERIAL | Cu | Zn | Ag | C |
|---|---|---|---|---|
| NUMBER OF SAMPLES | 58 | 20 | 10 | 20 |
| NUMBER OF TIME OF SOLIDIFICATION | 56 | 20 | 10 | 4 |
| SUPERCOOLING RELEASE RATE (%) | 97 | 100 | 100 | 20 |

FIG. 10

| ADDITIVE | RESULTS |
|---|---|
| BLANK | × |
| Cu PRODUCT | ○ |
| Ag PRODUCT | ○ |
| Zn PRODUCT | ○ |

FIG. 11

| ADDITIVE | PARTICLE DIAMETER | RESULTS |
|---|---|---|
| BLANK | — | × |
| Zn | 75–150 μm | ○ |
| Zn | LESS THAN 75 μm | ○ |
| Fe | 45 μm | ○ |
| Cu | 350 nm | ○ |
| Ag | 150 nm | ○ |
| $SiO_2$ | 5–15 nm | × |
| ZEOLITE | 75 μm | × |

SUPER-COOLING RELEASE MATERIAL AND METHOD FOR PRODUCING SAME

CROSS REFERENCE TO RELATED APPLICATIONS

This application is a U.S. National Phase Application under 35 U.S.C. 371 of International Application No. PCT/JP2015/005644 filed on Nov. 12, 2015 and published in Japanese as WO 2016/075941 A1 on May 19, 2016. This application is based on and claims the benefit of priority from Japanese Patent Application No. 2014-231287 filed on Nov. 14, 2014, No. 2015-105672 filed on May 25, 2015, and No. 2015-209259 filed on Oct. 23, 2015. The entire disclosures of all of the above applications are incorporated herein by reference.

TECHNICAL FIELD

The present disclosure relates to a supercooling release material which releases a supercooled state of a cold storage material and a method of producing the same.

BACKGROUND ART

It is known that a clathrate hydrate such as a TBAB hydrate to be generated by cooling a tetrabutylammonium bromide (TBAB) aqueous solution has a large heat density and is used as a cold storage material. In regard to such a clathrate hydrate, a single clathrate hydrate can be used as a heat storage material and multiple types of clathrate hydrates can be used as a heat storage material after being mixed with each other (see Patent Literature 1). However, the aqueous solution that generates a clathrate hydrate easily enters a supercooled state in which a hydrate is not generated even when the aqueous solution is cooled to a hydrate generation temperature or lower. Therefore, it is difficult to stably use the aqueous solution as a cold storage material.

Meanwhile, a technique of releasing the supercooled state by applying an electric field to a TBAB aqueous solution in the supercooled state has been reported (see Non Patent Literature 1). In this method, a mechanism in which a supercooling release material is generated in a portion of the TBAB aqueous solution to which the electric field is applied, generation of a crystal nucleus is supported by the supercooling release material to release the supercooled state, and then the supercooled state is gradually released from the portion for a crystal growth of a TBAB hydrate is assumed.

However, in the method described in Non Patent Literature 1, details of the supercooling release material to be generated in the case where the electric field is applied to the TBAB aqueous solution are unclear and reported cases having a description on what kind of a material the supercooled state of the TBAB aqueous solution is released by do not exist.

PRIOR ART LITERATURES

Patent Literature

Patent Literature 1: JP-2007-161893 A
Non Patent Literature 1: INTERNATIONAL JOURNAL OF REFRIGERATION 35 (2012) 1266-1274

SUMMARY

It is an object of the present disclosure to provide a supercooling release material which is capable of releasing a supercooled state of a cold storage material and a method of producing the same.

According to a first aspect of the present disclosure, a supercooling release material, which releases a supercooled state of a cold storage material including one or more types of alkylammonium halide aqueous solutions that generate a hydrate by being cooled to a hydrate generation temperature or lower, includes: an alkylammonium ion included in the cold storage material; and a metal halide ion which has, as a constituent element, a halogen element included in the cold storage material.

The supercooled state of the cold storage material can be reliably released by using the supercooling release material having such a configuration. When the configuration of the supercooling release material is specified, the supercooling release material can be generated not only by voltage application but also by organic synthesis.

According to a second aspect of the present disclosure, a method of producing a supercooling release material, which releases a supercooled state of a cold storage material including one or more types of alkylammonium halide aqueous solutions that generate a hydrate by being cooled to a hydrate generation temperature or lower, includes: applying a voltage to the alkylammonium halide aqueous solution. The supercooling release material includes an alkylammonium ion included in the cold storage material, and a metal halide ion which has, as a constituent element, a halogen element included in the cold storage material.

According to the method of producing a supercooling release material having such a configuration, the supercooled state of the cold storage material can be reliably released. When the configuration of the supercooling release material is specified, the supercooling release material can be generated not only by voltage application but also by organic synthesis.

According to a third aspect of the present disclosure, a method of producing a supercooling release material, which releases a supercooled state of a cold storage material including one or more types of alkylammonium halide aqueous solutions that generate a hydrate by being cooled to a hydrate generation temperature or lower, includes: adding at least one of single metals of Ag, Cu, Fe, and Zn to the cold storage material. The supercooling release material includes an alkylammonium ion included in the cold storage material, and a metal halide ion which has, as a constituent element, a halogen element included in the cold storage material.

According to the method of producing a supercooling release material having such a configuration, the supercooled state of the cold storage material can be reliably released. When the configuration of the supercooling release material is specified, the supercooling release material can be generated not only by voltage application but also by organic synthesis.

BRIEF DESCRIPTION OF DRAWINGS

The above and other objects, features and advantages of the present disclosure will become more apparent from the following detailed description made with reference to the accompanying drawings. In the drawings:

FIG. 6 is a diagram showing supercooling release rates, in a case where an electrode material of a voltage applying unit is changed, according to a second embodiment;

FIG. 10 is a diagram showing supercooling release effects, in a case where various additives are added to a TBAB aqueous solution, according to the third embodiment; and FIG. 11 is a diagram showing supercooling release effects, in a case where various additives are added to a TBAB aqueous solution, according to a sixth embodiment.

EMBODIMENTS

First Embodiment

Hereinafter, a first embodiment of the present disclosure will be described based on FIGS. 1 to 5.

Figure 1:
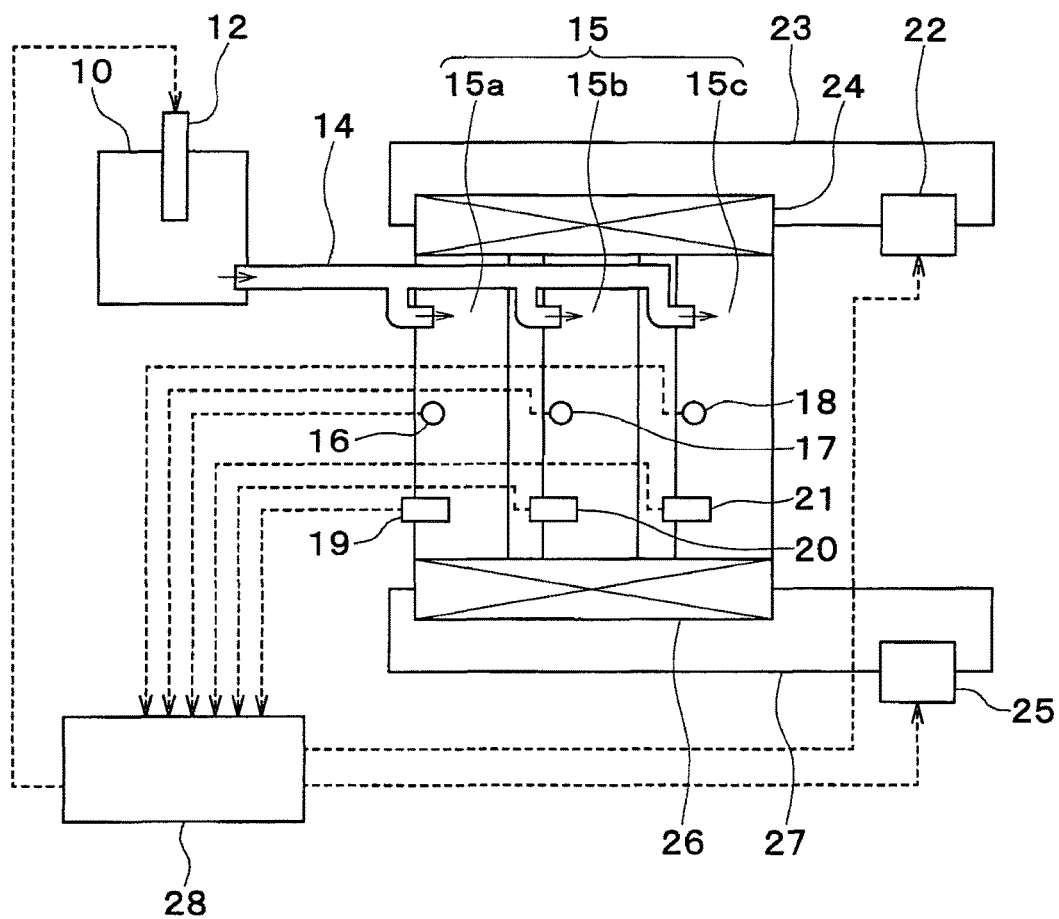
FIG. 1 is a conceptual view showing the overall configuration of a cold storage device according to a first embodiment.

As shown in FIG. 1, a cold storage device 1 of the present embodiment includes a supercooling release material generation unit 10, a cold storage material storing unit 15, a cold energy supply unit 22, a control unit 28, and the like.

A cold storage material is stored in the inside of the supercooling release material generation unit 10. An alkylammonium halide aqueous solution that generates a hydrate by being cooled to a hydrate generation temperature or lower is used as the cold storage material. In the present embodiment, a tetrabutylammonium bromide (TBAB) aqueous solution is used as an alkylammonium halide aqueous solution. Further, in the present embodiment, a TBAB aqueous solution of which the concentration is adjusted to 20 wt % is used as a cold storage material.

When the TBAB aqueous solution is cooled, a TBAB hydrate is generated in the aqueous solution and can be suitably used as a cold storage material that stores cold energy. The supercooling release material generation unit 10 is provided to generate a supercooling release material used for releasing the supercooled state of the TBAB aqueous solution. The supercooling release material will be described in detail later.

The supercooling release material generation unit 10 is provided with a voltage applying unit 12. The voltage applying unit 12 is provided to apply a voltage to the cold storage material and can be configured to circulate a current between a pair of electrodes provided at a predetermined interval. A supercooling release material is generated in the cold storage material of the supercooling release material generation unit 10 by applying a voltage to the cold storage material using the voltage applying unit 12. The voltage applying unit 12 of the present embodiment includes an electrode interval adjustment mechanism.

Figure 2:
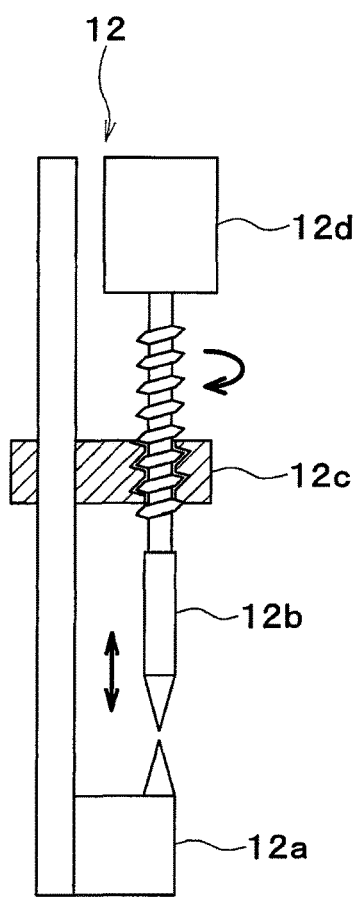
FIG. 2 is a conceptual view showing the configuration of an electrode of a voltage applying unit.

As shown in FIG. 2, the voltage applying unit 12 includes a pair of electrodes 12a and 12b, a fixing member 12c, and a motor 12d. The pair of electrodes 12a and 12b includes a fixed electrode 12a and a movable electrode 12b and the tips thereof face each other. A shaft portion of the movable electrode 12b is provided with a male screw portion and the fixing member 12c is provided with a female screw portion corresponding to the male screw portion of the movable electrode 12b.

In the present embodiment, the movable electrode 12b is an electrode connected to a positive side of a DC power supply (not illustrated) and the fixed electrode 12a is an electrode connected to a negative side of the DC power supply. In addition, a metal is used as the electrode material constituting the electrodes 12a and 12b. In the present embodiment, metal electrodes formed of Cu are used.

The movable electrode 12b is rotated by operating the motor 12d and the movable electrode 12b can be moved in a direction approaching the fixed electrode 12a or a direction away therefrom. In this manner, the voltage applying unit 12 is capable of adjusting the space between the fixed electrode 12a and the movable electrode 12b. Further, the distance between the fixed electrode 12a and the movable electrode 12b can be detected by, for example, measuring the resistance between the electrodes 12a and 12b.

Returning to FIG. 1, a cold storage material is stored in the cold storage material storing unit 15. The cold storage material storing unit 15 communicates with the supercooling release material generation unit 10 through a cold storage material pipe 14, and the cold storage material can flow between the supercooling release material generation unit 10 and the cold storage material storing unit 15. Further, the cold storage material storing unit 15 is disposed so as to be isolated from the supercooling release material generation unit 10 so that the influence of heat applied to each other can be suppressed as much as possible.

The cold storage material storing unit 15 is configured such that cold storage is made by cooling the cold storage material and generating a hydrate. The cold energy stored in the cold storage material in the cold storage material storing unit 15 can be utilized for, for example, air-cooling of an air conditioning apparatus.

The cold storage material storing unit 15 includes multiple (three in the present embodiment) storing units 15a, 15b, and 15c. Each of the storing units 15a, 15b, and 15c is connected to the supercooling release material generation unit 10 through the cold storage material pipe 14.

Temperature sensors 16, 17, and 18 for detecting the temperature of the cold storage material in the inside are respectively provided in each of the storing units 15a, 15b, and 15c. In addition, supercooling detection units 19, 20, and 21 for detecting the occurrence of the supercooled state of the cold storage material in the inside are respectively provided in each of the storing units 15a, 15b, and 15c.

For example, the supercooling detection units 19, 20, and 21 include a light emitting device and a light receiving device and may have a configuration of detecting the transmittance of light reaching the light receiving element from the light emitting element or a configuration of detecting scattered light using the light receiving element. Since the transmittance of light is decreased when the cold storage material is cooled and the proportion of the hydrate is increased, it can be determined that the cold storage material is in a supercooled state if the transmittance of light is greater than the reference value and the cold storage material is not in a supercooled state if the transmittance of light is lower than the reference value at a temperature lower than the hydrate generation temperature. Further, since light from the light emitting device is scattered when the cold storage material is cooled and the proportion of the hydrate is increased, it can be determined that the cold storage material is in a supercooled state if the scattered light cannot be detected and the cold storage material is not in a supercooled state if the scattered light is detected at a temperature lower than the hydrate generation temperature.

Alternatively, since the viscosity of the cold storage material becomes high when the cold storage material is cooled and the proportion of the hydrate is increased, the viscosity of the cold storage material may be detected by the supercooling detection units 19, 20, and 21. In this case, it is determined that the cold storage material is in a supercooled state if the viscosity of the cold storage material is lower than the reference value and the cold storage material is not in a supercooled state if the viscosity of the cold storage material is greater than the reference value at a temperature lower than the hydrate generation temperature.

Alternatively, since a change in heat quantity occurs due to phase change when the cold storage material is cooled and the hydrate is generated, the differential thermal may be detected using, for example, a thermocouple as the supercooling detection units 19, 20, and 21. In this case, it is determined that the cold storage material is in a supercooled state if the differential thermal detected by the supercooling detection units 19, 20, and 21 is lower than the reference value and the cold storage state is not in a supercooled state if the differential thermal detected by the supercooling detection units 19, 20, and 21 is greater than the reference value.

The cold energy supply unit 22 is configured such that a low-temperature refrigerant is supplied to a first heat exchanger 24 through a refrigerant pipe 23 and the cold storage material storing unit 15 is cooled. The cold energy supply unit 22 is configured as a known refrigeration cycle including, for example, a compressor, a condenser, and an expansion valve, and the first heat exchanger 24 can be used as an evaporator of the refrigeration cycle. The first heat exchanger 24 is in thermal contact with the cold storage material storing unit 15 and thus the cold storage material stored in the cold storage material storing unit 15 can be cooled by performing heat exchange between a low-temperature refrigerant supplied from the cold energy supply unit 22 and the cold storage material storing unit 15. That is, a "cooling device" includes the cold energy supply unit 22, the first heat exchanger 24, and the refrigerant pipe 23.

As shown in FIG. 1, the first heat exchanger 24 is disposed on the upper portion of the cold storage material storing unit 15. Since it is considered that heat storage materials not solidified in the cold storage material storing unit 15 are collected in the upper portion in the inside of the cold storage material storing unit 15, the heat storage materials can be efficiently coagulated by cooling the cold storage material storing unit 15 from the upper portion thereof.

Further, cold energy may be supplied from the cold energy supply unit 22 to the first heat exchanger 24 using the refrigerant pipe 23 described above as a device that supplies cold energy or a fluid having cold energy such as wind may be directly introduced into the first heat exchanger 24 from the cold energy supply unit 22.

The cold energy stored in the cold storage material of the cold storage material storing unit 15 is supplied to a cold energy utilizing unit 25 through a heat medium. The cold energy utilizing unit 25 can be used as, for example, an air conditioning apparatus and, for example, water can be used as a heat medium. A second heat exchanger 26 is provided so as to be in thermal contact with the lower portion of the cold storage material storing unit 15 and the second heat exchanger 26 performs heat exchange between the cold storage material storing unit 15 and the heat medium. The cold energy stored in the cold storage material of the cold storage material storing unit 15 can be supplied to the cold energy utilizing unit 25 by the heat medium, which has received the cold energy, flowing in the cold energy utilizing unit 25 through a heat medium pipe 27. Further, the cold energy utilizing unit 25, the second heat exchanger 26, and the heat medium pipe 27 correspond to a "cold energy utilizing device".

Further, since the specific gravity of hydrate crystals of a heat storage material is greater than water, it is considered that the hydrate crystals are collected in the lower portion in the inside of the cold storage material storing unit 15. Accordingly, the cold energy stored in the cold storage material of the cold storage material storing unit 15 can be efficiently utilized by providing the second heat exchanger 26 in the lower portion of the cold storage material storing unit 15.

Further, cold energy may be supplied from the second heat exchanger 26 to the cold energy utilizing unit 25 using the heat medium pipe 27 described above as a device that supplies cold energy or a fluid having cold energy such as wind may be directly introduced into the cold energy utilizing unit 25 from the second heat exchanger 26.

The control unit 28 includes a known microcomputer having a CPU, a ROM, a RAM, and the like and peripheral circuits and various calculation processes are performed based on an air conditioning control program stored in the ROM. Sensor signals from the temperature sensors 13, 16, 17, and 18 and the supercooling detection units 19, 20, and 21 are input to the control unit 28 and control signals are output to a temperature adjustment unit 11, the voltage applying unit 12, and the cold energy supply unit 22.

Figure 3:
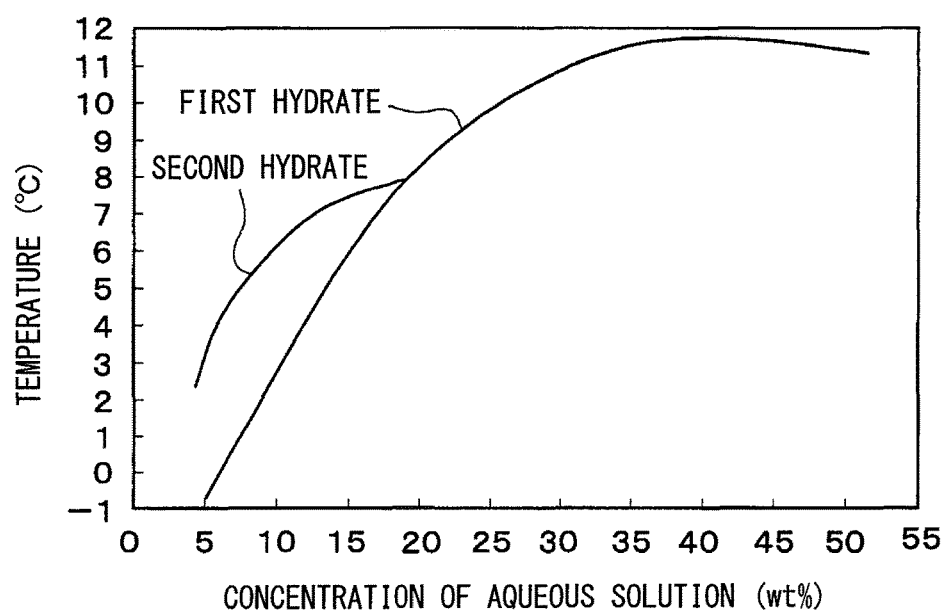
FIG. 3 is a graph showing the relationship between the concentration of a TBAB aqueous solution and the hydrate generation temperature.

Here, the TBAB aqueous solution used as the cold storage material in the present embodiment will be described. As shown in FIG. 3, two types of hydrates which are a first hydrate having a hydration degree of approximately 26 and a second hydrate having a hydration degree of approximately 38 are reported as typical hydrates of TBAB. The hydrate generation temperature varies depending on the type of hydrate or the concentration of the TBAB aqueous solution. Both of the first hydrate and the second hydrate may be generated in the TBAB aqueous solution of which the concentration is adjusted to 20 wt %, and the hydrate generation temperature is approximately 8° C. in both cases. The first hydrate is generated in the TBAB aqueous solution of which the concentration is adjusted to 40 wt % and the hydrate generation temperature is approximately 12° C.

In the section of the related art as described above, the TBAB aqueous solution has a property of easily entering the supercooled state in which a TBAB hydrate is not generated even when the TBAB aqueous solution is cooled to a temperature lower than the hydrate generation temperature. Therefore, in the cold storage device 1 of the present embodiment, it is restricted that the TBAB aqueous solution enters the supercooled state by generating the supercooling release material and uniformly supplying the supercooling release material to a desired portion.

In the present embodiment, the supercooling release material generated in the supercooling release material generation unit 10 is branched and supplied to each of multiple storing units 15a, 15b, and 15c through the cold storage material pipe 14. In this manner, the supercooling release material generated in the supercooling release material generation unit 10 can be uniformly diffused in and supplied to each of the storing units 15a, 15b, and 15c without being biased in a specific portion of the cold storage material storing unit 15.

Next, a supercooling release and control treatment performed by the cold storage device 1 having the above-described configuration will be described based on a flowchart of FIG. 4.

Figure 4:
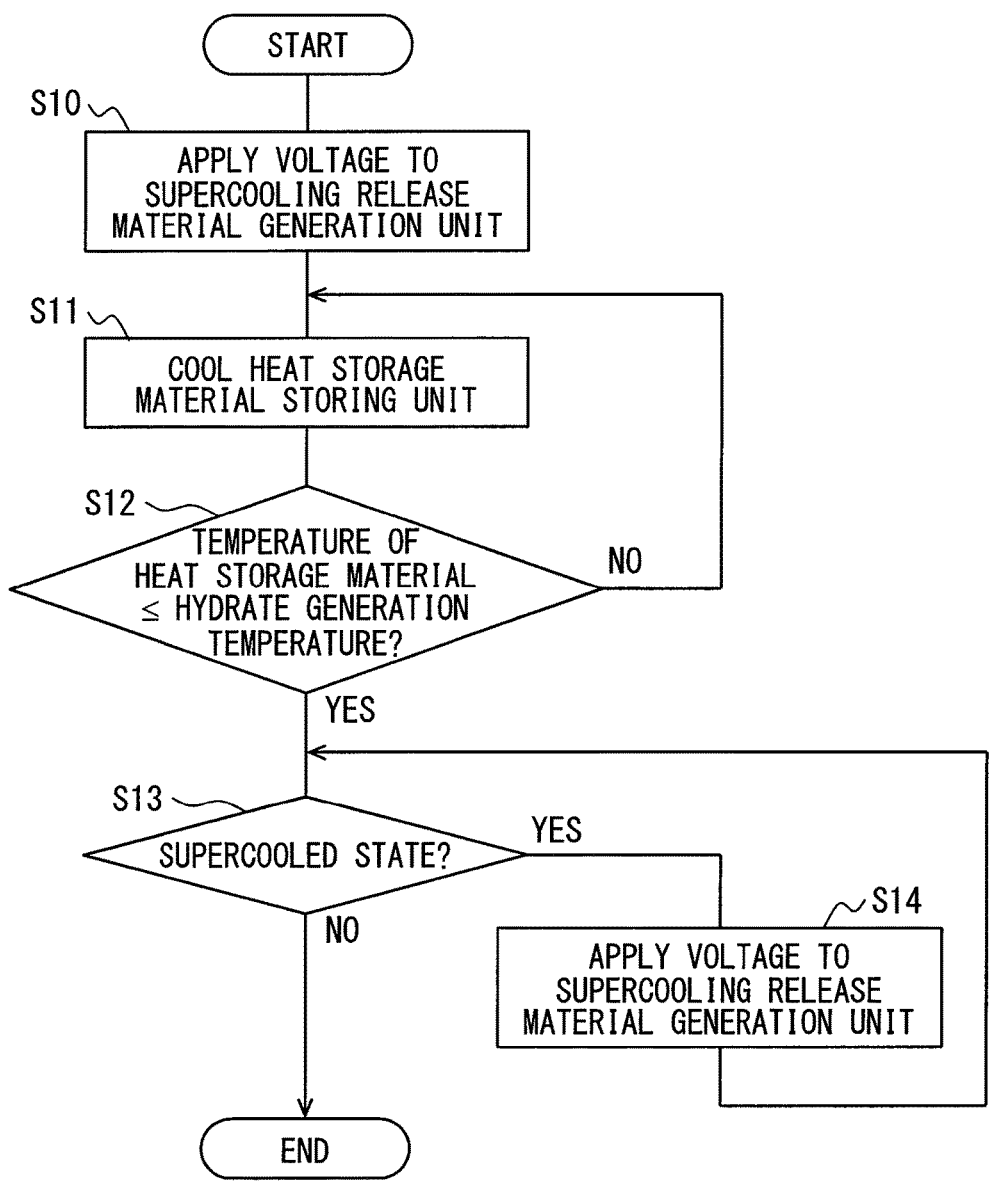
FIG. 4 is a flowchart showing a supercooling release and control treatment.

As shown in FIG. 4, first, a voltage is applied to the cold storage material of the supercooling release material generation unit 10 by the voltage applying unit 12 (S10). In this manner, a supercooling release material is generated in the inside of the supercooling release material generation unit 10. Further, the supercooling release material is supplied to the cold storage material of the cold storage material storing unit 15 through the cold storage material pipe 14.

Next, the cold storage material storing unit 15 is cooled by supplying a low-temperature refrigerant to the first heat exchanger 24 from the cold energy supply unit 22 (S11). Further, it is determined whether the cold storage material temperature of the cold storage material storing unit 15 is lower than or equal to the hydrate generation temperature based on the sensor signals from the temperature sensors 16 to 18 (S12).

As the result, in a case where it is determined that the cold storage material temperature is not lower than or equal to the hydrate generation temperature (S12: NO), the process returns to S11. Meanwhile, in a case where it is determined that the cold storage material temperature is lower than or equal to the hydrate generation temperature (S12: YES), it is determined that the cold storage material of the cold storage material storing unit 15 has entered the supercooled state based on the sensor signals from the supercooling detection units 19, 20, and 21 (S13).

As the result, it is determined that the cold storage material has entered the supercooled state (S13: YES), a voltage is applied to the cold storage material of the supercooling release material generation unit 10 by the voltage applying unit 12 (S14). In this manner, a supercooling release material is generated in the inside of the supercooling release material generation unit 10. Further, the supercooling release material is supplied to the cold storage material of the cold storage material storing unit 15 through the cold storage material pipe 14.

Further, as the result of the determination process at S13, the supercooling release and control treatment is finished in a case where it is determined that the cold storage material is not in the supercooled state (S13: NO).

Here, the supercooling release material generated by the supercooling release material generation unit 10 of the present embodiment will be described. In the present embodiment, the supercooling release material is extracted from the TBAB aqueous solution including the supercooling release material generated by the supercooling release material generation unit 10 through voltage application performed by the voltage applying unit 12 during the following process.

First, the TBAB aqueous solution including the supercooling release material generated by applying a voltage is extracted from the supercooling release material generation unit 10 and then suctioned and filtered using an omnipore membrane filter (manufactured by Merch Millipore Corporation, pore size: 0.45 μm), thereby obtaining a water-insoluble material. The material is subjected to a drying treatment at 25° C. for 12 hours using a vacuum drier. Here, AVO-200NB (manufactured by AS ONE Corporation) is used as a drier and GLD-051 (manufactured by ULVAC, Inc.) is used as a vacuum pump.

Next, the material after the drying treatment is mixed with chloroform and stirred and then suctioned and filtered using an omnipore membrane filter (manufactured by Merch Millipore Corporation, pore size: 0.45 μm) again, thereby obtaining a chloroform-insoluble material. The material is subjected to a drying treatment at 25° C. for 12 hours using a vacuum drier and then a target supercooling release material is obtained.

The chemical structure of the supercooling release material obtained in the above-described extraction process is specified as follows by the mass spectrometry using a matrix-assisted laser desorption ionization method.

MALDI-TOF MASS (BRUKER DALTONICS, autoflex) is used as an analysis device. The measurement is carried out under conditions in which $N_2$ laser (wavelength: 337 nm) is used as a laser light source, the measured mass is set to be in a range of 20 to 3000 (m/z), and the cumulative number is set to 1000.

Figure 5:
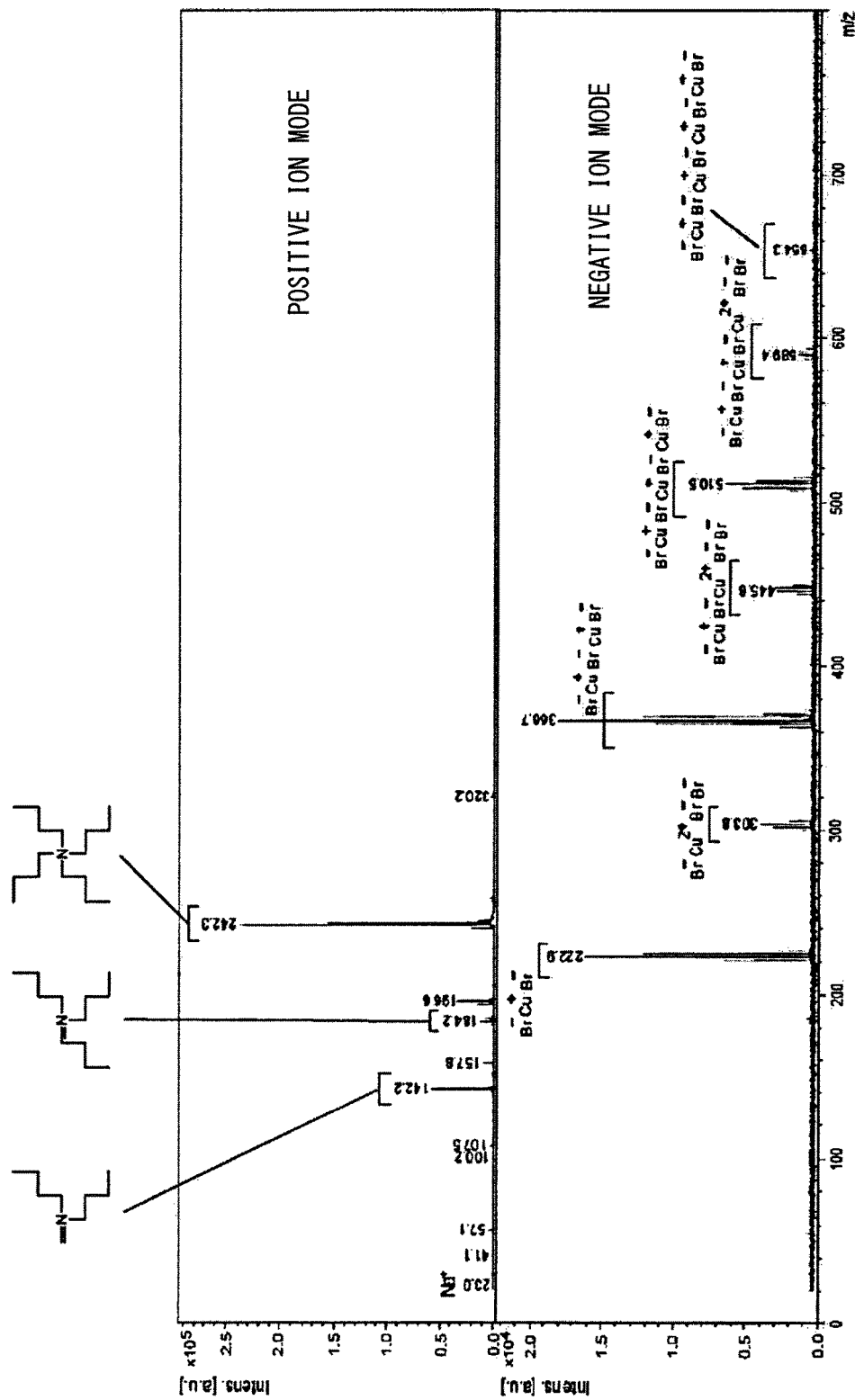
FIG. 5 is a diagram showing a mass spectrum which is an analysis result of a supercooling release material.

As analysis results, the mass spectrum of cations shown in the upper part of FIG. 5 and the mass spectrum of anions shown in the lower part of FIG. 5 are obtained.

From the mass spectrum in the upper part of FIG. 5, it is understood that the supercooling release material includes tetrabutylammonium ions ($TBA^+$) represented by Formula (1) as cations. The tetrabutylammonium ions are derived from tetrabutylammonium bromide (TBAB) which is a cold storage material.

[Chem 1]

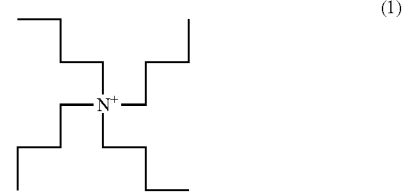

(1)

The cations included in the supercooling release material may be alkylammonium ions including at least four hydrocarbon groups having 1 to 7 carbon atoms. The four hydrocarbon groups may be the same as or different from each other. Examples of the hydrocarbon group include methyl (n=1), ethyl (n=2), n-propyl (n=3), iso-propyl (n=3), n-butyl (n=4), iso-butyl (n=4), n-pentyl (n=5), iso-pentyl (n=5), n-hexyl (n=6), iso-hexyl (n=6), n-heptyl (n=7), and iso-heptyl (n=7).

From the mass spectrum in the lower part of FIG. 5, it is understood that the supercooling release material includes at least copper bromide ions represented by Formula (2) as anions.

[Chem 2]

(2)

Further, the anions included in the supercooling release material may include copper bromide ions having at least any of the combinations [$Br^-$, $Cu^+$], [$Br^-$, $Cu^{2+}$], and [$Br^-$, $Cu^+$, $Cu^{2+}$]. Cu included in the copper bromide ions is derived from a Cu electrode and Br included in the copper bromide ions is derived from tetrabutylammonium bromide (TBAB) serving as a cold storage material. Hereinafter, anions formed of a combination including metal ions and halide ions are collectively referred to as metal halide ions. In this case, the valence or the number of ions constituting those and the valence of all anions are not limited.

From the description above, it can be specified that the supercooling release material includes a material represented by Formula (3).

[Chem 3]

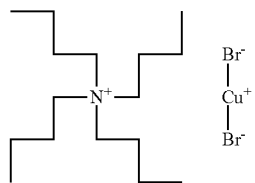

(3)

In the present embodiment described above, a voltage is applied to the cold storage material of the supercooling release material generation unit 10 by the voltage applying unit 12. In this manner, the supercooling release material can be generated by the supercooling release material generation unit 10 according to the necessity and the supercooled state of the cold storage material can be effectively restricted when the cold storage material is cooled to the hydrate generation temperature or lower by the cold storage material storing unit 15 communicating with the supercooling release material generation unit 10.

In the present embodiment, the chemical structure of a material as one of multiple constituent components in the supercooling release material generated by applying a voltage to the TBAB aqueous solution can be specified. In this manner, it is possible to clarify the type of material which is capable of releasing the supercooled state of the TBAB aqueous solution.

In the present embodiment, the first heat exchanger 24 used for cooling the heat storage material of the cold storage material storing unit 15 is disposed in the upper portion of the cold storage material storing unit 15. In this manner, the heat storage material collected in the upper portion of the cold storage material storing unit 15 without being solidified can be efficiently coagulated by being cooled from the upper portion of the cold storage material storing unit 15.

In the present embodiment, the second heat exchanger 26 used for receiving cold energy of the heat storage material of the cold storage material storing unit 15 is disposed in the lower portion of the cold storage material storing unit 15. In this manner, the cold energy of the heat storage material collected in the lower portion of the cold storage material storing unit 15 by being solidified can be efficiently received from the lower portion of the cold storage material storing unit 15.

Second Embodiment

Next, a second embodiment of the present disclosure will be described. In the second embodiment, the same parts as the first embodiment will not be repeatedly described and only different parts will be described.

In the second embodiment, multiple types of materials are used as electrode materials of a voltage applying unit 12 and a supercooling release treatment is repeatedly performed on a TBAB aqueous solution using the respective electrode materials. The supercooling release treatment is performed by the procedures described with reference to the flowchart of FIG. 4 in the first embodiment. Further, the supercooling release rate of each electrode material is calculated by measuring the number of times of solidification of the TBAB aqueous solution due to the supercooling release treatment for each electrode material. In the second embodiment, Cu, Zn, Ag, and C are used as the electrode materials of the voltage applying unit 12. Further, the cooling temperature of the cold storage material is 5° C.

As shown in FIG. 6, the supercooling release rate in a case where a Cu electrode is used is 97%, the supercooling release rate in a case where a Zn electrode is used is 100%, and the supercooling release rate in a case where a Ag electrode is used is 100%. In other words, high supercooling release effects are obtained in a case where any metal electrode from among Cu, Zn, and Ag is used. Meanwhile, the supercooling release rate in a case where a C electrode, which is a non-metal electrode, is used is 20%, and the supercooling release effects are low.

Since the analysis results of the material generated in the TBAB aqueous solution through voltage application using the Cu electrode have been described in the first embodiment with reference to FIG. 5, analysis results of a material generated in the TBAB aqueous solution through voltage application using the Zn electrode and the Ag electrode will be described in the second embodiment. The mass spectrometry is carried out by the same procedures as described in the first embodiment.

First, the analysis results obtained by performing the mass spectrometry on the material generated in the TBAB aqueous solution through voltage application using the Zn electrode will be described with reference to FIG. 7.

Figure 7:
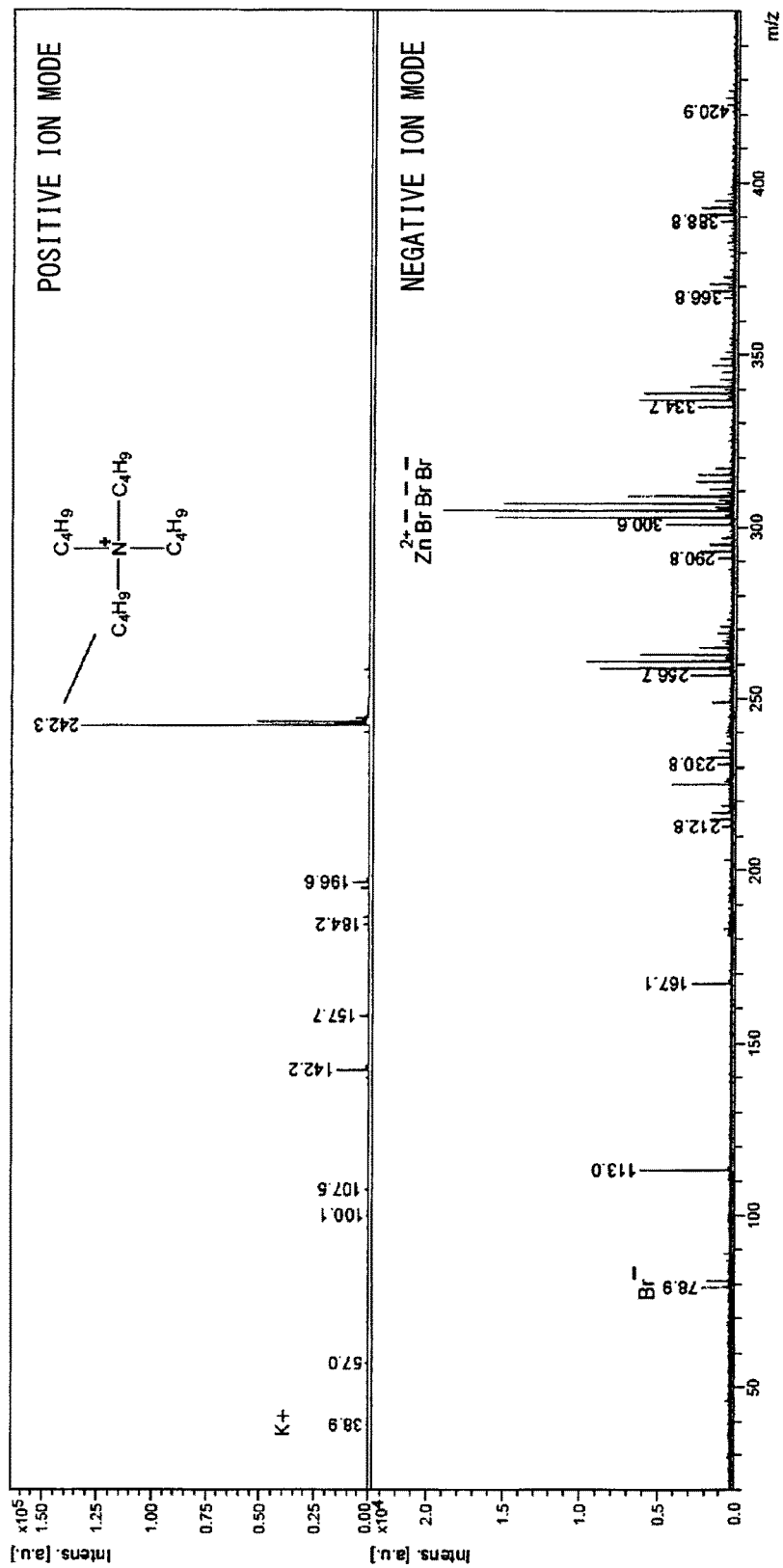
FIG. 7 is a diagram showing a mass spectrum which is an analysis result of a supercooling release material generated when a Zn electrode is used.

From the mass spectrum in the upper part of FIG. 7, it is understood that the supercooling release material includes tetrabutylammonium ions (TBA$^+$) represented by Formula (1) as cations. From the mass spectrum in the lower part of FIG. 7, it is understood that the supercooling release material includes zinc bromide ions represented by [Zn$^{2+}$, Br$^-$, Br$^-$, and Br$^-$] as anions.

It is understood that the supercooling release material includes a Zn complex based on these combinations.

Next, the analysis results obtained by performing the mass spectrometry on the material generated in the TBAB aqueous solution through voltage application using the Ag electrode will be described with reference to FIG. 8.

Figure 8:
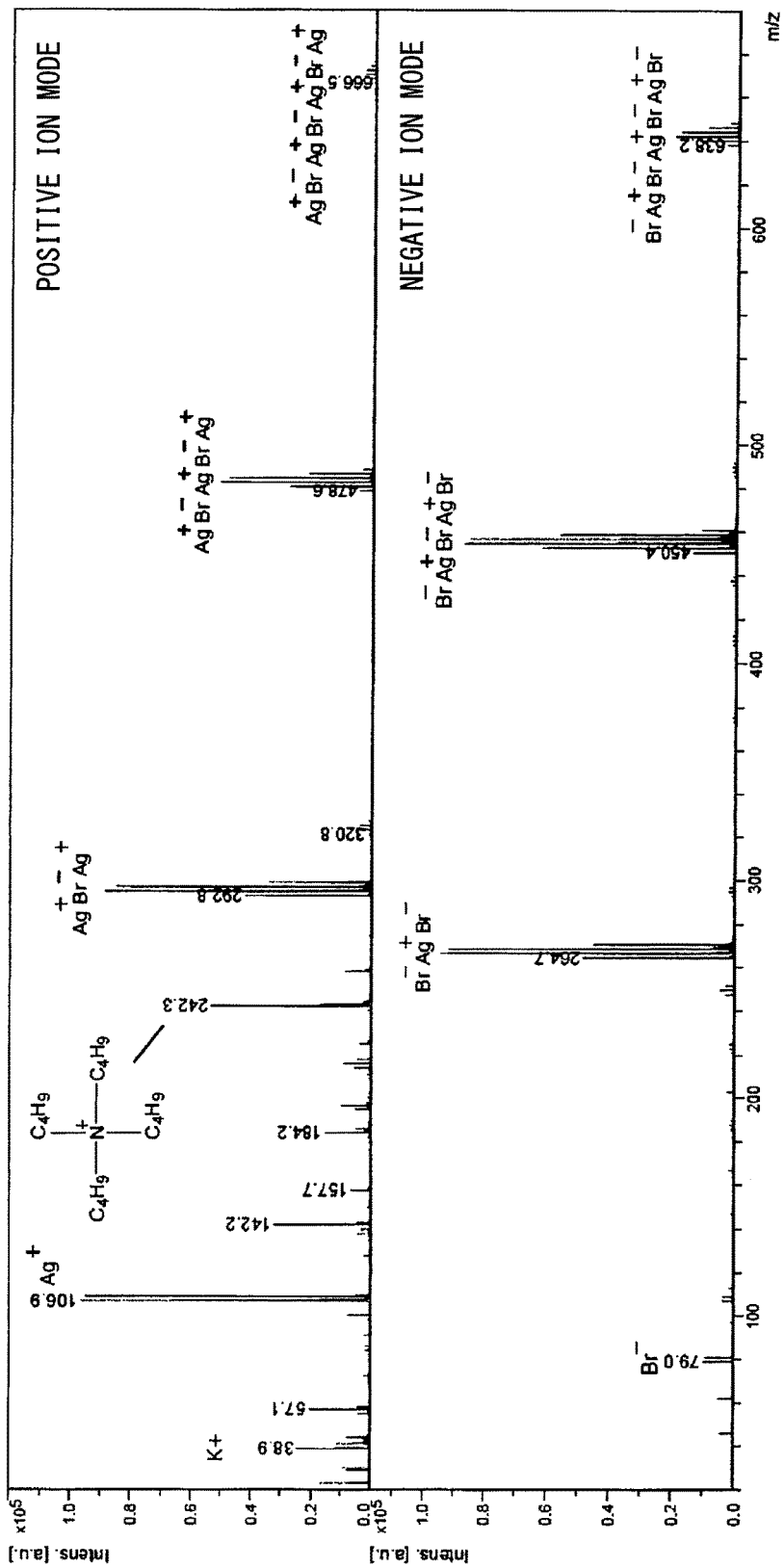
FIG. 8 is a diagram showing a mass spectrum which is an analysis result of a supercooling release material generated when a Ag electrode is used.

From the mass spectrum in the upper part of FIG. 8, it is understood that the supercooling release material includes tetrabutylammonium ions (TBA$^+$) represented by Formula (1) as cations and Ag$^+$ (or [Ag$^+$, Br$^-$, ..., Ag$^+$]). Further, from the mass spectrum in the lower part of FIG. 8, it is understood that the supercooling release material includes Br$^-$ (or [Br$^-$, Ag$^+$, ..., Br$^-$]) as anions. From the combination of silver bromide ions represented by tetrabutylammonium ions (TBA+) as cations and [Br$^-$, Ag$^+$, ..., Br$^-$] as anions, it is understood that the supercooling release material includes a Ag complex.

According to the second embodiment described above, the supercooling release effects can be highly obtained in a case where any metal from among Cu, Zn, and Ag is used as the electrode material of the voltage applying unit 12.

In the second embodiment, it is shown that the configuration of the supercooling release material to be generated is changed by changing the electrode material of the voltage applying unit 12. For example, a supercooling release material which includes tetrabutylammonium ions (TBA$^+$) as cations and copper bromide ions as anions is generated in a case where a Cu electrode is used. Further, a supercooling release material which includes TBA$^+$ as cations and zinc bromide ions as anions is generated in a case where a Zn electrode is used. Further, a supercooling release material which includes TBA$^+$ as cations and silver bromide ions as anions is generated in a case where a Ag electrode is used.

That is, the supercooling release material which includes TBA$^+$ as cations and copper bromide ions as anions has been described in the first embodiment. Meanwhile, according to the second embodiment, it is shown that the supercooling release effects of the TBAB aqueous solution are obtained even in a case where the supercooling release material includes metal bromide ions other than copper bromide ions such as silver bromide ions or zinc bromide ions as anions.

Further, as described above, a mass peak derived from a metal bromide as an anion is confirmed from the analysis result obtained by performing the mass spectrometry on the material generated in the TBAB aqueous solution in a case where any metal from among Cu, Zn, and Ag is used as the electrode material of the voltage applying unit 12. Further, TBA$^+$ which is an ammonium ion included in the TBAB aqueous solution is detected from the cations. From these results, metal bromide ions generated by voltage application performed by the voltage applying unit 12 and a compound formed of alkylammonium ions are considered to have supercooling release effects with respect to the TBAB aqueous solution.

In general, the state of a d-orbit of a metal element in a complex is referred to as structure selection energy and it is known that the structure selection energy is closely related with the coordinate structure of the complex. Therefore, materials in the similar state of the d-orbit frequently have physical properties or chemical properties similar to each other.

In the second embodiment, a metal element that is confirmed to make a complex having supercooling release effects occasionally enters a closed shell state in which the d-orbit is filled with ten electrons when the metal element has become an ion. Examples of such elements include Cd and Au in addition to Cu, Ag, and Zn.

Further, the state in which the d-orbit has five electrons is referred to as a semi-closed shell state and known to have characteristics similar to those of the closed shell state. Examples of such elements include Fe, Cr, Mn, Co, Ni, Mo, Tc, Ru, Rh, Re, Os, Ir, and Pt. Therefore, a complex formed of bromide ions and tetrabutylammonium ions of these metal elements, in addition to the complex confirmed as described above, is highly likely to have supercooling release effects with respect to the TBAB aqueous solution.

From the results described above, as the metal elements constituting the supercooling release material, metals in which the d-orbit easily enters the closed shell state when the metal elements have become ions or metals in which the d-orbit easily enters the semi-closed shell state when the metal elements have become ions can be used. Specifically, as the metal elements constituting the supercooling release material, at least any of the metal element of Cu, Ag, Zn, Cd, Au, Cr, Mn, Fe, Co, Ni, Mo, Tc, Ru, Rh, Re, Os, Ir, and Pt can be used.

In the second embodiment, the chemical reaction of generating the supercooling release material is accelerated by applying a voltage to the TBAB aqueous solution using the voltage applying unit 12 and providing electric energy from the outside. In other words, it is considered that the target material can be obtained by adding single bodies of metals constituting the supercooling release material to a cold storage material in advance without applying a voltage to the TBAB aqueous solution.

In the second embodiment, a compound having tetrabutylammonium ions is obtained by applying a voltage to a cold storage material including tetrabutylammonium ions (TBA$^+$). In a case where the same operation is performed on a cold storage material including ammonium ions different from tetrabutylammonium ions, a compound having the ammonium ions is generated and this material is considered to have supercooling release effects.

Third Embodiment

Next, a third embodiment of the present disclosure will be described. In the third embodiment, the same parts as each of the above-described embodiment will not be repeatedly described and only different parts will be described.

The cold storage device 1 of the first embodiment is configured such that the supercooling release material is generated in the inside of the supercooling release material generation unit 10 by applying a voltage to the TBAB aqueous solution using the supercooling release material generation unit 10. Meanwhile, in the third embodiment, a supercooling release material is generated in the outside of a cold storage device 1.

Figure 9:
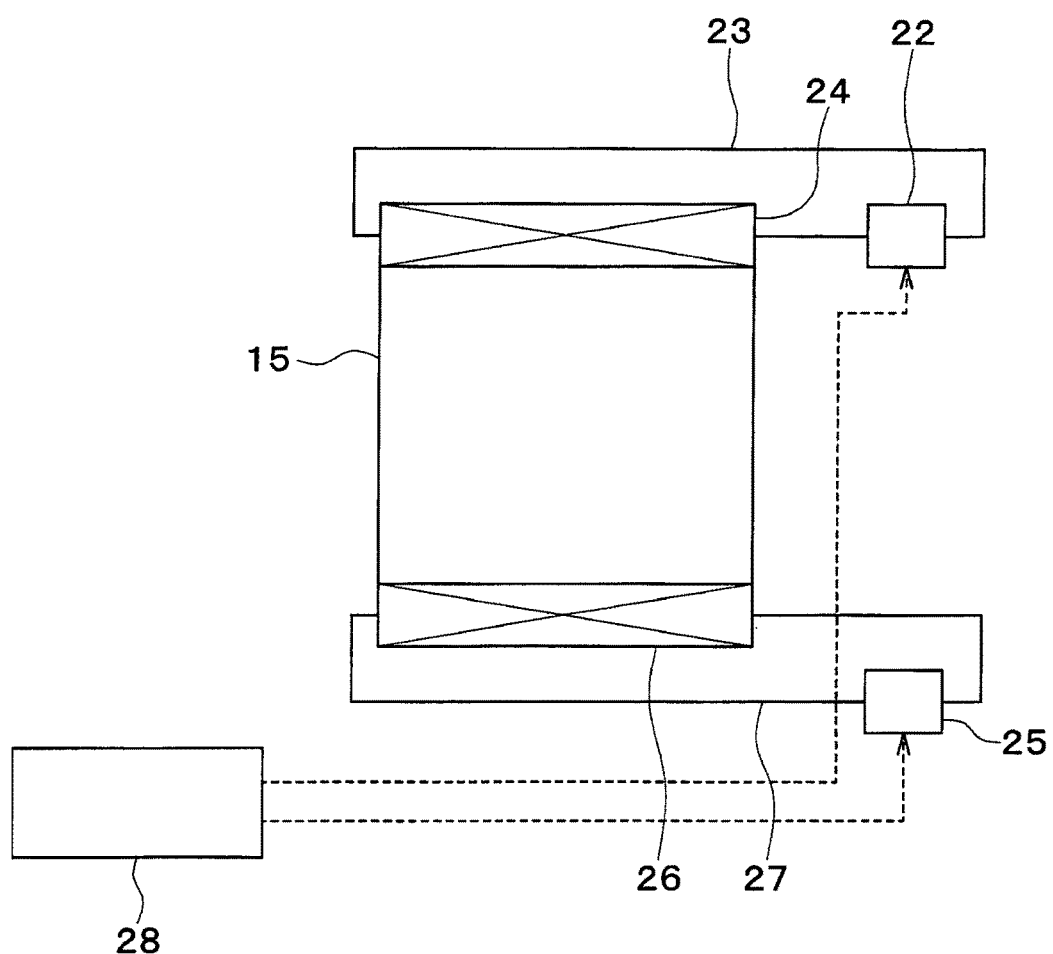
FIG. 9 is a conceptual view showing the overall configuration of a cold storage device according to a third embodiment.

As shown in FIG. 9, the cold storage device 1 of the third embodiment includes a cold storage material storing unit 15, a cold energy supply unit 22, and a control unit 28. The cold storage device 1 of the third embodiment is not provided with a supercooling release material generation unit 10. The cold storage material storing unit 15 of the third embodiment is formed as one container and the inside thereof is filled with a TBAB aqueous solution as a cold storage material. The supercooling release material generated in the outside of the cold storage device 1 is added to the cold storage material.

The supercooling release material is generated by an external voltage applying device (not illustrated). The external voltage applying device has the same configuration as the configuration of the supercooling release material generation unit 10 provided in the cold storage device 1 of the first and second embodiments. The voltage applying device is provided with an electrode for applying a voltage to the cold storage material. The supercooling release material is generated by applying a voltage to the cold storage material using the voltage applying device.

In the third embodiment, the supercooling release effects in a case where the supercooling release material generated in the outside is added to the cold storage material are evaluated. A TBAB aqueous solution of which the concentration is adjusted to 40 wt % is used as the cold storage material. The hydrate generation temperature of the TBAB aqueous solution of which the concentration is adjusted to 40 wt % is approximately 12° C. Each product in a case where Cu, Ag, and Zn are used by the external voltage applying device as electrode materials is used as an additive to be added to the cold storage material. A product obtained through voltage application is extracted by the procedures described in the first and second embodiments. In FIG. 10, a product obtained through voltage application using a Cu electrode is referred to as a "Cu product", a product obtained through voltage application using a Ag electrode is referred to as a "Ag product", and a product obtained through voltage application using a Zn electrode is referred to as a "Zn product".

A solution obtained by adding 0.01 wt % of the additive to the cold storage material is allowed to stand in a thermostat of which the temperature is set to 5° C., and the supercooling release effects are evaluated. In FIG. 10, a case where hydrate crystals are visually observed within 24 hours after the start of cooling is shown by "○" and a case where hydrate crystals are not visually observed during that time is shown by "×".

As shown in FIG. 10, a cold storage material is solidified in a case where a Cu product, a Ag product, and a Zn product are added to the cold storage material. Meanwhile, a cold storage material is not solidified in a case where these products are not added to the cold storage material. From this result, it is confirmed that the material generated by applying a voltage to the TBAB aqueous solution has supercooling release effects.

According to the configuration of the third embodiment, generation of a crystal nucleus is supported by adding the supercooling release material, which is already generated by applying a voltage to the cold storage material, to the cold storage material in a case where the cold storage material enters the supercooled state. Therefore, it is expected to generate a nucleus having a critical crystal nucleus diameter or greater in a short time. As the result, it is possible to reliably release the supercooled state of the cold storage material.

In the third embodiment, the supercooling release material generated by voltage application in the outside of the cold storage device 1 is added to the cold storage material in advance. Accordingly, it is not necessary to provide the voltage applying unit 12 as in the first embodiment in the cold storage device 1 of the third embodiment and the supercooled state of the cold storage material can be reliably released with a simple configuration.

Fourth Embodiment

Next, a fourth embodiment of the present disclosure will be described. In the fourth embodiment, the same parts as each of the above-described embodiment will not be repeatedly described and only different parts will be described.

A difference between the third embodiment and the fourth embodiment is that the supercooling release material is generated by organic synthesis or the like in the fourth embodiment. A cold storage device 1 of the fourth embodiment has the same configuration as the configuration of the cold storage device 1 of the third embodiment shown in FIG. 9.

In the fourth embodiment, the supercooling release material generated by organic synthesis or the like in advance is added to a cold storage material of a cold storage material storing unit 15. The supercooling release material of the fourth embodiment is a material (that is, a compound formed of copper bromide ions and tetrabutylammonium ions) having the chemical structure represented by Formula (3) of the first embodiment and is reported in "Acta Chemica Scandinavica B37 (1983), p. 57 to 62".

In the fourth embodiment, the supercooling release material having the above-described chemical structure is organically synthesized according to the method described in "Acta Chemica Scandinavica B36 (1982), p. 125 and 126". It is confirmed that the target material is obtained by performing the mass spectrometry.

Further, a TBAB aqueous solution of which the concentration is adjusted to 20 wt % is used as the cold storage material. The hydrate generation temperature of the TBAB aqueous solution of which the concentration is adjusted to 20 wt % is approximately 8° C. A solution obtained by adding 0.01 wt % of the supercooling release material obtained by synthesis to the cold storage material is allowed to stand in a thermostat of which the temperature is set to 1° C., and the supercooling release effects are evaluated. After the start of cooling, hydrate crystals are visually observed within 24 hours. Meanwhile, hydrate crystals are not visually observed in a case where the compound is not added. In this manner, it is confirmed that the synthesized compound has the supercooling release effects.

According to the configuration of the fourth embodiment, generation of a crystal nucleus is supported by the supercooling release material by adding the supercooling release material, which has the chemical structure represented by Formula (3), to the cold storage material in advance in a case where the cold storage material enters the supercooled state. Therefore, it is expected to generate a nucleus having a critical crystal nucleus diameter or greater in a short time. As the result, it is possible to reliably release the supercooled state of the cold storage material.

In the fourth embodiment, the supercooling release material generated by organic synthesis is added to the cold storage material in advance. Accordingly, it is not necessary to provide the voltage applying unit 12 as in the first embodiment in the cold storage device 1 of the fourth embodiment and the supercooled state of the cold storage material can be reliably released with a simple configuration.

Fifth Embodiment

Next, a fifth embodiment of the present disclosure will be described. In the fifth embodiment, the same parts as each of the above-described embodiment will not be repeatedly described and only different parts will be described.

In the fifth embodiment, the type of supercooling release material to be synthesized is different from that of the fourth embodiment. In the fifth embodiment, a compound formed of silver bromide ions and tetrabutylammonium ions is synthesized by the following procedures.

First, 0.36 g (that is, 3 mmol) of KBr is added to 90 mL of dimethylformamide (DMF) and then the mixture is stirred. 0.56 g (that is, 3 mmol) of AgBr is added to the mixture in a darkroom and the mixture is stirred for 30 minutes. The insoluble matter is filtered using a membrane filter having a pore size of 0.5 μm, thereby obtaining a filtrate. A solution obtained by dissolving 1.93 g (that is, 6 mmol) of TBAB in 100 mL of EtOH is separately adjusted. The filtrate and the solution are mixed with each other.

Precipitated single yellow powder is filtered using a membrane filter having a pore size of 0.5 μm and washed with EtOH, thereby obtaining 245 mg of single yellow powder (yield: 9.8%). It is confirmed that the target material is obtained by performing the mass spectrometry.

A TBAB aqueous solution of which the concentration is adjusted to 40 wt % is used as the cold storage material. The hydrate generation temperature of the TBAB aqueous solution of which the concentration is adjusted to 40 wt % is approximately 12° C. A solution obtained by adding 0.01 wt % of the synthesized material to the cold storage material is allowed to stand in a thermostat of which the temperature is set to 9° C., and the supercooling release effects are evaluated. After the start of cooling, hydrate crystals are visually observed within 24 hours. Meanwhile, hydrate crystals are not visually observed in a case where the compound is not added. In this manner, it is confirmed that the synthesized compound has the supercooling release effects.

Even in the fifth embodiment described above, the same effects as in the fourth embodiment can be obtained.

Sixth Embodiment

Next, a sixth embodiment of the present disclosure will be described. In the sixth embodiment, the same parts as each of the above-described embodiment will not be repeatedly described and only different parts will be described.

A cold storage device 1 of the sixth embodiment has the same configuration as the configuration of the cold storage device of the third embodiment shown in FIG. 9. Further, in the sixth embodiment, a supercooling release material formed of any single metal from among Zn, Fe, Cu, and Ag is added to a cold storage material of a cold storage material storing unit 15.

In the sixth embodiment, supercooling release effects are evaluated by adding these single metals, and $SiO_2$ and zeolite, as a comparative example, to the cold storage material. Further, a TBAB aqueous solution of which the concentration is adjusted to 20 wt % is used as the cold storage material. The hydrate generation temperature of the TBAB aqueous solution of which the concentration is adjusted to 20 wt % is approximately 8° C. Zn having a particle diameter of less than 75 μm and a particle diameter of 75 to 150 μm, Fe having a particle diameter of 45 μm, Cu having a particle diameter of 350 nm, Ag having a particle diameter of 150 nm, $SiO_2$ having a particle diameter of 5 to 15 nm, and zeolite having a particle diameter of 75 μm) are used as additives to be added to the cold storage material.

A solution obtained by adding 0.01 wt % of the additive to the cold storage material is allowed to stand in a thermostat of which the temperature is set to 1° C., and the results are shown in FIG. 11. In FIG. 11, a case where hydrate crystals are visually observed within 24 hours after the start of cooling is shown by "○" and a case where hydrate crystals are not visually observed during that time is shown by "x".

As shown in FIG. 11, it is confirmed that Zn, Fe, Cu, and Ag have the supercooling release effects even in a case where single metals are added to the cold storage material. Further, since the supercooling release effects are not seen from $SiO_2$ and zeolite which have the same diameter as these metals, it is evident that the effects are not from addition of simple fine particles.

In the first and second embodiments, it is considered that a reaction of generating the supercooling release material in a solution progresses and thus the supercooling release effects are obtained in the case where these single metals are added on the analogy of the case where a voltage is applied using the voltage applying unit 12. That is, the single metals become metal bromide ions together with Br included in the TBAB aqueous solution serving as a cold storage material and the metal bromide ions function as the supercooling release material together with $TBA^+$ included in the TBAB aqueous solution serving as a cold storage material.

According to the configuration of the sixth embodiment described above, generation of a crystal nucleus is supported by the supercooling release material by adding the supercooling release material, which is formed of any single metal from among Cu, Ag, Zn, and Fe, to the cold storage material in advance in a case where the cold storage material enters the supercooled state. Therefore, it is expected to generate a nucleus having a critical crystal nucleus diameter or greater in a short time. As the result, it is possible to reliably release the supercooled state of the cold storage material using the supercooling release material formed of single metals which are easily obtained.

Seventh Embodiment

Next, a seventh embodiment of the present disclosure will be described. In the seventh embodiment, the same parts as each of the above-described embodiment will not be repeatedly described and only different parts will be described.

In each embodiment described above, an alkylammonium halide aqueous solution formed of tetrabutylammonium bromide (TBAB) is singly used as a heat storage material, but multiple types of alkylammonium halide aqueous solutions are mixed with each other and then used as a heat storage material (hereinafter, also referred to as a mixed cold storage material) in the seventh embodiment.

In the case where multiple types of alkylammonium halide aqueous solutions are mixed with each other and used as a mixed heat storage material, when some alkylammonium halide hydrates included in the mixed heat storage material are crystallized antecedently, crystallization of other alkylammonium halides is induced and the entire mixed cold storage material is solidified.

Meanwhile, when alkylammonium halide hydrates expected to be crystallized antecedently in the mixed cold storage material enters the supercooled state, the supercooling release effects are not exhibited and the entire mixed cold storage material is likely to enter the supercooled state. In this case, a state in which the performance of the cold storage material is not exhibited at all may occur. For this reason, in the seventh embodiment, the supercooling release material is added to the mixed cold storage material and the supercooled state of the mixed cold storage material is released.

The supercooling release material used for the mixed cold storage material may have the supercooling release effects with respect to at least one alkylammonium halide aqueous solution included in the mixed cold storage material. When the supercooled state of some alkylammonium halide aqueous solutions included in the mixed cold storage material can be released so that the alkylammonium halide aqueous solutions are solidified, it is considered that solidified alkylammonium halide hydrates induce solidification of other alkylammonium halide aqueous solutions and the entire mixed cold storage material can be solidified.

A cold storage device 1 of the seventh embodiment has the same configuration as the configuration of the cold storage device of the third embodiment shown in FIG. 9. In the seventh embodiment, a tri-n-butyl-n-pentylammonium bromide (TBPAB) aqueous solution of which the concentration is adjusted to 34 wt % and a tetrabutylammonium bromide (TBAB) aqueous solution of which the concentration is adjusted to 40 wt % are prepared as a cold storage material.

The hydrate generation temperature of the TBPAB aqueous solution of which the concentration is adjusted to 34 wt % is approximately 6° C. and the hydrate generation temperature of the TBAB aqueous solution of which the concentration is adjusted to 40 wt % is approximately 12° C. Therefore, the hydrate generation temperature of a cold storage material can be adjusted by mixing two types of aqueous solutions with each other.

In the seventh embodiment, an aqueous solution obtained by mixing the TBPAB aqueous solution and the TBAB aqueous solution described above at a weight ratio of 9:1 is used as a mixed cold storage material. Further, the Ag product described in the third embodiment is used as an additive. The Ag product is a product obtained by voltage application using a Ag electrode.

A solution obtained by adding 0.01 wt % of the above-described additive to the mixed cold storage material is allowed to stand in a thermostat of which the temperature is set to 5° C., and then evaluation is performed. In a case where the Ag product is added to the mixed cold storage material, all samples are solidified within 24 hours after the start of cooling. Meanwhile, in a case where the Ag product is not added to the mixed cold storage material, hydrate crystals are not confirmed even after the lapse of 24 hours from the start of cooling. Since the Ag product has the supercooling release effects with respect to the TBAB aqueous solution, it is considered that crystallization of a TBAB hydrate induces crystallization of a TBPAB hydrate and thus the entire mixed cold storage material is solidified.

Other Embodiments

For example, the TBAB aqueous solution is used as a heat storage material in the first to sixth embodiments and a mixed solution of the TBAB aqueous solution and the TBPAB aqueous solution is used as a heat storage material in the seventh embodiment, but alkylammonium halide aqueous solutions other than the TBAB aqueous solution and the TBPAB aqueous solution can be used as a heat storage material. These alkylammonium halide aqueous solutions may be respectively and individually used as a heat storage material or multiple types of alkylammonium halide aqueous solutions are mixed with each other and then used as a heat storage material.

Further, in the first embodiment described above, the voltage applying unit 12 is disposed in the supercooling release material generation unit 10 provided by being isolated from the heat storage material storing unit 15, but the disposition is not limited thereto. For example, the voltage applying unit 12 may be disposed in the heat storage material storing unit 15 without providing the supercooling release material generation unit 10.

In the third to seventh embodiments, the supercooling release material is added to the cold storage material of the cold storage material storing unit 15, but the configuration is not limited thereto. For example, the supercooling release material is provided on the inner wall surface of the cold storage material storing unit 15 and then the cold storage material may be put into the cold storage material storing unit 15.

In the second embodiment described above, the example in which any metal from among Cu, Zn, and Ag is used as the electrode material of the voltage applying unit 12 has been described, but a metal other than these metals may be used as the electrode material of the voltage applying unit 12.

Further, each of the embodiments described above, an example in which the pair of electrodes 12a and 12b of the voltage applying unit 12 are configured of the same type of metal electrode has been described, but the present invention is not limited thereto as long as at least a metal electrode is used for the movable electrode 12b. Hereinafter, this point will be described.

When a voltage is applied to the TBAB aqueous solution by the voltage applying unit 12, an oxidation-reduction reaction occurs in the electrodes 12a and 12b. An oxidation reaction occurs in the movable electrode 12b, which is connected to the positive side of a DC power supply, between these electrodes 12a and 12b. When a metal is used as the electrode material of the movable electrode 12b, the metal becomes ions and then is melted in an aqueous solution. Since the metal ions serve as the constituent elements of the supercooling release material, it is necessary to use a metal for at least the movable electrode 12b in order to generate the supercooling release material through voltage application. Meanwhile, the fixed electrode 12a connected to the negative side of the DC power supply is not necessarily a metal electrode because the metal constituting the electrode is not ionized.

It is noted that a flowchart or the processing of the flowchart in the present application includes sections (also referred to as steps), each of which is represented, for instance, as S10. Further, each section can be divided into several sub-sections while several sections can be combined into a single section. Furthermore, each of thus configured sections can be also referred to as a device, module, or means.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

What is claimed is:

1. A supercooling release material which releases a supercooled state of a cold storage material including one or more types of alkylammonium halide aqueous solutions that generate a hydrate by being cooled to a hydrate generation temperature or lower, the supercooling release material comprising:
   an alkylammonium ion included in the cold storage material; and
   a metal halide complex ion which has, as a constituent element, a halogen element included in the cold storage material, wherein:
   a metal element included in the metal halide complex ion is at least one of Cu, Ag, Zn, Cd, Au, Cr, Mn, Fe, Co, Ni, Mo, Tc, Ru, Rh, Re, Os, Ir, and Pt.

2. The supercooling release material according to claim 1, wherein:
   the alkylammonium ion is represented by a formula of $[N(C_nH_{2n+1})_4]^+$; and
   n represents one of 1 to 7.

3. The supercooling release material according to claim 1, wherein:
   the halogen element constituting the metal halide complex ion is Br.

4. The supercooling release material according to claim 1, wherein:
   the alkylammonium halide includes tetrabutylammonium bromide.

5. A method of producing a supercooling release material which releases a supercooled state of a cold storage material including one or more types of alkylammonium halide aqueous solutions that generate a hydrate by being cooled to a hydrate generation temperature or lower, wherein:
   the supercooling release material includes an alkylammonium ion included in the cold storage material, and a metal halide complex ion which has, as a constituent element, a halogen element included in the cold storage material, wherein:

a metal element included in the metal halide complex ion is at least one of Cu, Ag, Zn, Cd, Au, Cr, Mn, Fe, Co, Ni, Mo, Tc, Ru, Rh, Re, Os, Ir, and Pt, the method comprising:

applying a voltage to the alkylammonium halide aqueous solution.

6. The method of producing a supercooling release material according to claim 5, wherein:

the voltage is applied to the alkylammonium halide aqueous solution by a pair of electrodes, the pair of electrodes is provided in a supercooling release material generation unit into which the cold storage material is introduced to generate the supercooling release material; and the electrode material is one of Cu, Ag, Zn, Cd, Au, Cr, Mn, Fe, Co, Ni, Mo, Tc, Ru, Rh, Re, Os, Ir, and Pt.

7. A method of producing a supercooling release material which releases a supercooled state of a cold storage material including one or more types of alkylammonium halide aqueous solutions that generate a hydrate by being cooled to a hydrate generation temperature or lower, wherein:

the supercooling release material includes an alkylammonium ion included in the cold storage material, and a metal halide complex ion which has, as a constituent element, a halogen element included in the cold storage material, wherein:

a metal element included in the metal halide complex ion is at least one of Cu, Ag, Zn, Cd, Au, Cr, Mn, Fe, Co, Ni, Mo, Tc, Ru, Rh, Re, Os, Ir, and Pt, the method comprising:

adding at least one of single metals of Ag, Cu, Fe, and Zn to the cold storage material.

8. The method of producing a supercooling release material according to claim 5, wherein:

the alkylammonium ion is represented by a formula of $[N(C_nH_{2n+1})_4]^+$; and n represents one of 1 to 7.

9. The method of producing a supercooling release material according to claim 5, wherein:

the halogen element constituting the metal halide complex ion is Br.

10. The method of producing a supercooling release material according to claim 5, wherein:

the alkylammonium halide includes tetrabutylammonium bromide.

* * * * *